United States Patent [19]

Yamashita

[11] Patent Number: 5,260,763
[45] Date of Patent: Nov. 9, 1993

[54] INSTRUMENT FOR OBSERVING JEWELS' BRILLIANCE AS DIAMOND, AND METHOD OF TAKING PHOTOGRAPHS WITH SAID INSTRUMENT

[75] Inventor: Kinsaku Yamashita, Tokyo, Japan

[73] Assignee: Masayo Yamashita, Tokyo, Japan

[21] Appl. No.: 582,859

[22] PCT Filed: Feb. 16, 1990

[86] PCT No.: PCT/JP90/00188
§ 371 Date: Oct. 15, 1990
§ 102(e) Date: Oct. 15, 1990

[87] PCT Pub. No.: WO90/09577
PCT Pub. Date: Aug. 23, 1990

[30] Foreign Application Priority Data

Feb. 17, 1989 [JP] Japan ................ 1-37949
Feb. 15, 1990 [JP] Japan ................ 2-32399

[51] Int. Cl.⁵ .......................... G01N 21/87
[52] U.S. Cl. ...................... 356/30; 359/804
[58] Field of Search ........... 356/30; 359/804, 801

[56] References Cited

U.S. PATENT DOCUMENTS

| | | | |
|---|---|---|---|
| 1,744,485 | 1/1930 | Michel et al. | 356/30 |
| 3,410,634 | 11/1968 | Buckner | 359/804 |
| 3,740,142 | 6/1973 | Takubo | 356/30 |
| 3,867,032 | 2/1975 | Bruck | 356/30 |
| 3,885,242 | 5/1975 | Duran | 354/296 |
| 3,989,379 | 11/1976 | Eickhorst | 356/30 |
| 4,647,194 | 3/1987 | Shigetomi et al. | 356/30 |
| 4,906,083 | 3/1990 | Sattler | 350/524 |
| 5,045,688 | 9/1991 | Domenico et al. | 250/223 B |

FOREIGN PATENT DOCUMENTS

| | | |
|---|---|---|
| 3600115 | 7/1987 | Fed. Rep. of Germany . |
| 66855 | 5/1979 | Japan . |
| 158937 | 12/1981 | Japan . |
| 148123 | 9/1982 | Japan . |
| 109041 | 7/1985 | Japan . |

*Primary Examiner*—Richard A. Rosenberger
*Attorney, Agent, or Firm*—Nields & Lemack

[57] ABSTRACT

The present invention relates to an instrument for observing the brilliance of jewels, especially of diamonds, and a method of photographing them with this instrument. The instrument of this invention is composed of a lower tubular portion comprising a non-transparent material and an upper tubular portion comprising a semi-transparent material, and a magnifying observation lens can be furnished on the upper end part of said upper tubular portion in accordance with using purposes of the instrument. The semi-transparent upper tubular portion can move slidably with respect to the lower tubular portion. The diamond is positioned on a placing part within the lower tubular portion, and an observer studies it from the upper end part of the upper tubular portion. According to this instrument, the semi-transparent upper tubular portion adjusts appropriately the light directing to the diamond, and as a result, it is possible to observe characteristic patterns corresponding to the diamond brilliance. Further, the photographing method of this invention is to take photographs of diamonds within the lower tubular portion with a camera from the upper side of the upper tubular portion of the instrument, and it serves to judge the diamond brilliance more clearly than the conventional photographs of diamonds.

53 Claims, 10 Drawing Sheets

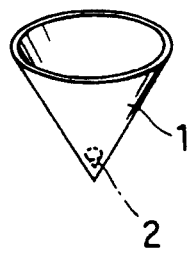
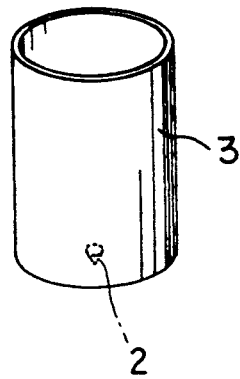
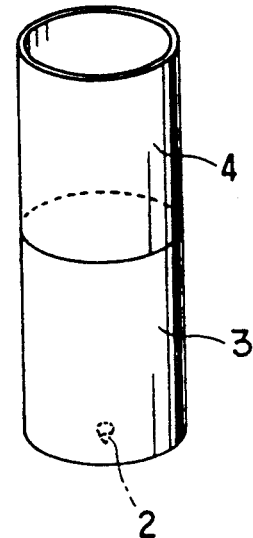
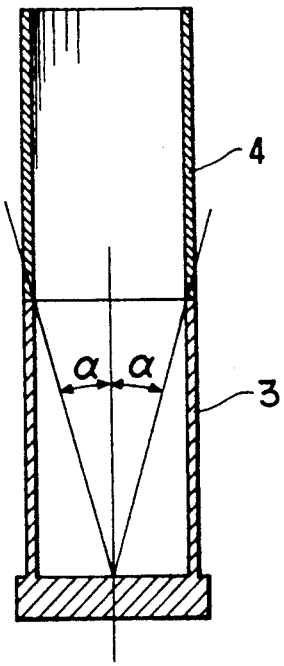
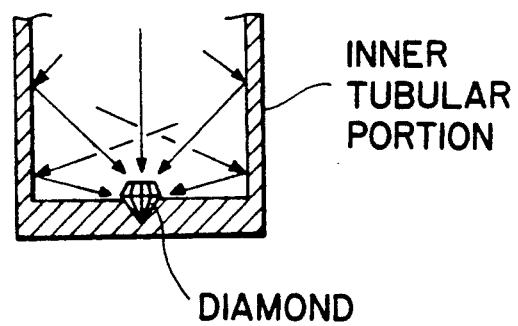

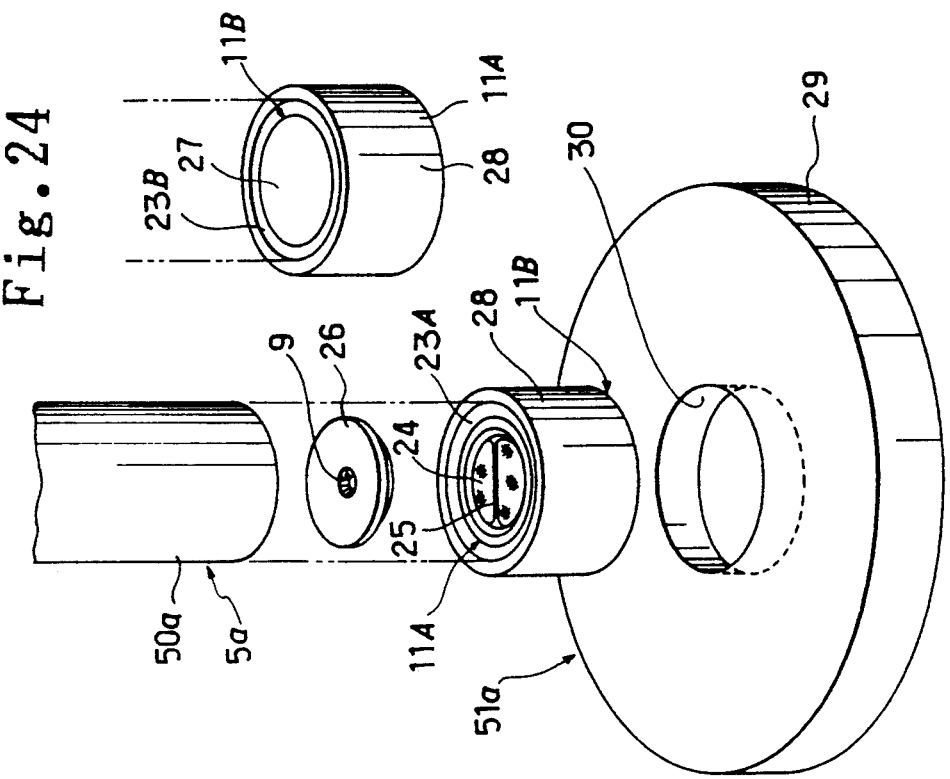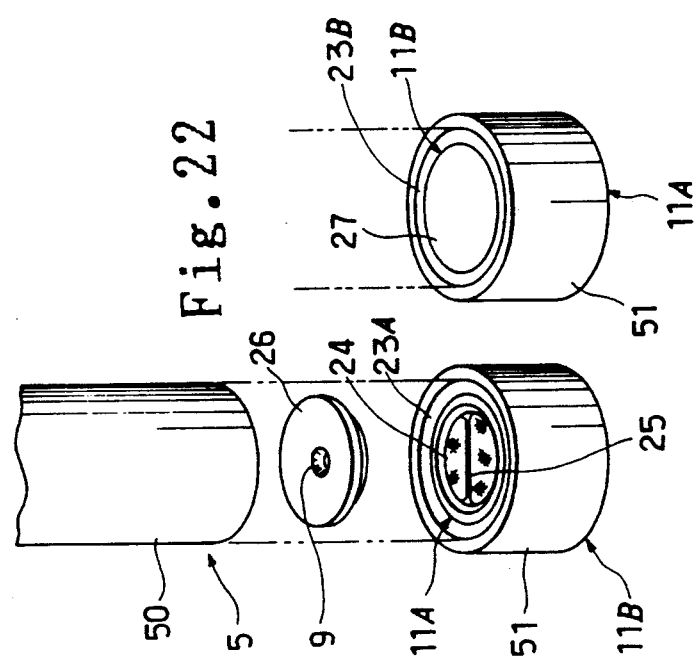

INSTRUMENT FOR OBSERVING JEWELS' BRILLIANCE AS DIAMOND, AND METHOD OF TAKING PHOTOGRAPHS WITH SAID INSTRUMENT

TECHNICAL FIELD

The present invention relates to an instrument for observing brilliance of jewels, especially of diamonds, and a method of taking photographs of them with this instrument.

TECHNICAL BACKGROUND

One of the reasons why diamonds are so popular as jewels consists in their inimitable brilliance. The brilliance peculiar to the diamond occurs in that a light going into a diamond causes internal reflections at its cut sides, and the reflecting lights are gathered at the table side (surface). Accordingly, the degree of the diamond brilliancy is largely influenced by cuttings and proportions of the diamond.

Diamonds of ideal brilliant cut pursuing brilliancy have proportions cutting off superfluous parts, and each of the cut faces look to the proper direction respectively. Thus, a major part of the light incident in the diamond regularly effects the internal reflections and is gathered on the table side, so that the greatest brilliancy is available.

On the other hand, diamonds which are roughly cut based only on carat (size) have proportions leaving extra excrescence and the cut surfaces face in random directions. Therefore the incident light cannot make regular internal reflections, and the amount of the light gathered on the table side is small and less brilliant. Further if the cut is very bad, some of the incident light passes through the rear side (pavilion) of the diamond without reflecting.

In shops, general purchasers normally observe diamonds with the naked eye, and the diamonds look almost the same in shining due to the illuminations or the like there, irrespective of good and bad cuts, and thus it is very difficult for purchasers without professionally trained eyes to distinguish between good cuts and bad ones.

Therefore, such the general trend is that are based more upon manufactures and sales attention to the carats which directly reflects on the prices than to the qualities of the cut and the proportions which are difficult to judge.

An instant observing instrument of the diamond brilliancy has been proposed in Japanese Utility Model Laid Open 60-109041, in which a diamond is placed between a magnifying glass and a light source, and a light from the source is applied to a red disc having a hole at its center and equipped to the side of an object lens of the magnifying glass so as to reflect the light against the diamond, whereby the diamond with much red light may be judged as having good brilliancy.

However, since said instrument needs a light source, it can be used only at places with electric sources, and is not handy. In addition, diamond patterns observed with this instrument are composed only of a white and a red of one kind (lighting parts are red and non lightening parts are white), and are particularly monotone. Light and shade of the patterns which are effected by strength and weakness of the light required to judge the diamond brilliancy, are not seen at all, and do not bring about steroscopic effect. The diamond brilliancy cannot be therefore judged fully and clearly.

The photographs used for professional opinions of diamonds and others are prepared by applying the illumination to the diamond from its downward direction and taking photographs with a camera from its upward side. The patterns photographed thereby appear such that the most brilliant parts and the least brilliant parts when viewed with the naked eye are blackish, and parts whitish. Such photographs are as follows:

1) Parts which should be seen most brilliant are taken black as if negative films of monochromes, 2) Since the most brilliant parts and the least brilliant parts are both taken black, it could not be discriminated which parts are really lighting, and 3) The parts to be taken white must include more brilliant and less brilliant parts than those inherently photographed ones, that is, strong and weak brightness, but the above stated photographs scarcely have light and shade variation caused by differences in brightness. So the brightness difference in the white parts cannot be distinguished at all.

Thus, the patterns do not produce a stereoscopic effect.

Non-professionals could not easily distinguish them, while the specialists could distinguish them somehow or other.

The present invention has been realized in view of these conventional problems, and the first object of this invention is to offer an instrument with which non-professionals can easily distinguish the good and bad brilliance of jewels as diamonds, and which is of a simple structure without requiring a light source, and is portable.

The second object of this invention is to offer a photographing method by means of the above mentioned instrument.

DISCLOSURE OF THE INVENTION

Thus, the observing instrument according to the present invention has the structure as mentioned below.

(1) An observing instrument of jewels' brilliance as diamonds, composed of:

a lower tubular portion comprising a material not permitting the passage of light, an inner bottom portion of which is a placing part of a jewel to be observed, an upper tubular portion whose main body comprises a semi-transparent substance, and which is to be positioned on the upper part of said lower tubular portion, and an observation magnifying lens to be mounted on the upper end part of said upper tubular portion, wherein the surface of the inner bottom part of said lower tubular portion is black or blackish color with less light reflection.

(2) The instrument in the above (1), wherein the lower tubular portion is composed such that a combining line between the center of the inner bottom part of the lower tubular portion and an upper edge part thereof has an angle from 10° to 25° with respect to the axial line of the lower tubular portion.

(3) The instrument in the above (1) or (2), wherein the lower tubular portion is composed of a base part, the upper surface of which is for placing a jewel thereon, and a tubular body which is detachably attached on the upper part of said base part.

(4) The instrument in the above (1), (2) or (3), wherein an entire part of an upper tubular portion or at least an upper part thereof is structured in a conical-trapezoidal shape, and a lower end thereof is connected to a short tubular part of a large diameter or a brim part, which is continued to the upper part of the lower tubular portion, and the inner bottom surface of said short tubular part or the upper surface of said brim part is composed in black or blackish color with less light reflection.

(5) An observing instrument of jewels' brilliance as diamonds, composed of:

an outer tubular portion comprising a material not permitting the passage of light, an inner bottom portion of which is a placing part of a jewel to be observed, an inner tubular portion whose main body comprises a semi-transparent substance, and which is inserted slidably vertically into the interior of said outer tubular portion from the upper end thereof, and an observation magnifying lens to be mounted on the upper end part of said inner tubular portion, wherein a surface of the inner bottom portion of said outer tubular portion is black or blackish color with less light reflection.

(6) The instrument in the above (5), wherein the outer tubular portion is composed such that a combining line between the center of the inner bottom part of the outer tubular portion and the upper edge portion thereof has an angle from 10° to 25° with respect to the axial line of the outer tubular portion.

(7) The instrument in the above (5) or (6), wherein the outer tubular portion is composed of a base part, the upper surface of which is a part for placing a jewel thereon and a tubular body which is detachably attached on the upper part of said base part.

(8) An observing instrument of jewels' brilliance as diamonds, composed of:

a lower tubular portion comprising a material not permitting the passage of light, an inner bottom part of which is a placing part of a jewel to be observed, and an upper tubular portion whose main body comprises a semi-transparent substance, and which is to be positioned on the upper part of said lower tubular portion, wherein the surface of the inner bottom part of said lower tubular portion is black or blackish color with less light reflection.

(9) The instrument in the above (8), wherein the lower tubular portion is composed such that a combining line between the center of the inner bottom part of the lower tubular portion and the upper edge portion thereof has an angle from 10° to 25° with respect to the axial line of the lower tubular portion.

(10) The instrument in the above (8) or (9), wherein the lower tubular portion is composed of a base part, the upper surface of which is a placing part of a jewel thereon and a tubular body which is detachably attached on the upper part of said base part.

(11) The instrument in the above (8), (9) or (10), wherein an entire part of an upper tubular portion or at least an upper part thereof is structured in a conical-trapezoidal shape, and a lower end thereof is connected to a short tubular part of a large diameter or a brim part, which is continued to the upper part of the lower tubular portion, and the inner bottom surface of said short tubular part or the upper surface of said brim part is composed in black or a blackish color with less light reflection.

(12) The instrument in the above (8), (9), (10) or (11), wherein a camera rest having a penetrating hole at the center thereof is connected to the upper end part of the upper tubular portion, and at least the circumferential part around the penetrating hole on the upper surface of said camera rest is composed in black or a blackish color with less light reflection.

(13) The instrument in the above (8), (9) or (10), wherein the upper tubular portion is structured to be larger in diameter than the lower tubular portion; the lower end thereof is connected to the short tubular part of a large diameter or the brim part mounted on the upper part of the lower tubular portion; a camera rest having a penetrating hole at its center is connected on the upper end part of the upper tubular portion; the inner bottom surface of said short tubular part or the upper surface of the brim part are composed in black or a blackish color with less light reflection; at least a circumferential part around the penetrating hole at the upper surface of said camera rest is composed in black or a blackish color with less light reflection; and the underside surface of said camera rest is composed in white or a high bright color.

(14) An observing instrument of jewels' brilliance as diamonds, composed of:

an outer tubular portion comprising a material not permitting the passage of light, an inner bottom portion of which is a placing part of jewel to be observed, and an inner tubular portion whose main body comprises a semi-transparent substance, and which is inserted slidably vertically into the interior of said outer tubular portion from the upper end thereof, wherein a surface of the inner bottom portion of said outer tubular portion is black or blackish color with less light reflection.

(15) The instrument in the above (14), wherein the outer tubular portion is composed such that a combining line between the center of the inner bottom part of the lower tubular portion and the upper edge part thereof has an angle from 10° to 25° with respect to the axial line of the lower tubular portion.

(16) The instrument in the above (14) or (15), wherein the outer tubular portion is composed of a base part, the upper surface of which is a placing part of a jewel thereon and a tubular body which is detachably attached on the upper part of said base part.

The photographing method according to the present invention has compositions as mentioned below.

(I) A method of photographing jewels as diamonds by means of the observing instrument as described above by positioning a jewel on the placing part of a lower tubular portion or an outer tubular portion, and directing the lens of a photographing machine to the jewel on the placing part from the upper direction of the upper tubular portion or the inner tubular portion so as to take photographs of the jewels.

(II) The method in the above (I) by means of the observing instrument as described in (12) or (13), by positioning the jewel on the placing part of the lower tubular portion, and applying the lens of the photographing machine to the penetrating hole of the camera rest so as to take photographs of the jewel.

In the above mentioned structure, it is desirable that the inner circumference of the lower tubular portion or the outer tubular portion is black or blackish color with less light reflection, otherwise in a chromatic color as red. In particular, the latter chromatic color is preferable for judging clearly the diamond brilliancy as mentioned later.

The brilliancy proper to the diamond is made both by the surface reflection and the inner reflection. The surface reflection appears even in the glass or like, but in regard to the diamond, since there are many chances that the light incident from the surface thereof is refracted at the cut faces of its bottom and reflects, the brilliance peculiar to the diamond appears. The volume of the inner reflection depends upon the cuts and the proportions as stated above, so the cuts, and proportions are of the most importance for obtaining the most brilliancy.

When the diamonds are observed with the naked eye through the instrument of the present invention, the diamonds are placed on the placing part of the lower tubular portion thereof (explanation will be made hereinafter with an example of the instrument provided with the lower tubular portion and the upper tubular portion), and they are observed from the upper end part of the upper tubular portion.

The light goes into the lower tubular portion composed of the non-transparent material from the upper end part of the upper tubular portion as well as from the tubular body composed of the semi-transparent material, and it collides against the diamonds. A part of the light reflects at the side of the table surface, and another part thereof makes the inner reflections at the cut faces and is returned in the direction of the table surface, and the other part passes through to the placing part due to the cutting qualities of the diamonds. The light reflecting on the table surface and the light gathered in the direction of the table by the inner reflection come to the observer's eyes.

FIG. 1(A) and (B) are photographs of diamonds which may be seen with the naked eye, observing the diamonds by placing the table surface upward, by means of the inventive instrument where the inner circumference of the lower tubular portion thereof is colored red.

As apparently seen from these photographs, using the instrument of the invention, it is possible to observe very characteristic patterns corresponding to the reflecting lights from the diamonds. The diamond shown in (A) of these photographs has the almost ideal brilliant cut with much volume of the inner reflection of an light, and it is very brilliant when it is seen with the naked eye. The pattern of the diamond shown in the photograph (A) is composed of a white color and some kinds of red colors (grey in the attached photograph) differing in brightness and color tone. The white is a part where the light directly incident into the diamond reflects and comes back as it is; the light red (pink) is a mixture of the reflection of the direct light incident with the diamond and the light incident into the diamond after reflecting at the inner circumference of the lower tubular portion (the light reflecting at the lower tubular portion); the vivid red is a part where the reflecting light at said lower tubular portion reflects in the diamond and comes back as it is; and the deep red (rouge) is a part where the volume of the inner reflection in the diamond of the incident reflecting light at the lower tubular portion is less and seen by mixing with other a color (black) on the placing part. That is, the above mentioned reference signifies that, among the patterns observed, the white part indicates the most volume of the inner reflection, and as the red becomes deeper, the volume of the inner reflection becomes small. If the reflection volume is small, the black color of the foundation of the diamond placing part is seen as a deep red. But since the inner reflections occur in almost all of the cut sides in the diamond of this photograph (A), the configuration of the diamond itself is very clear, and besides there are as a whole a large proportion of the white and a bright red.

In addition, as seen from the photograph, in the diamond of the brilliant cut having the ideal proportions, white "arrows" radially extending in eight directions from its center are clearly acknowledged.

On the other hand, the photograph of FIG. 1(B) is an example observing the diamond which is roughly cut and undesirable in proportions, having a small proportion of the white parts as a whole in comparison with the diamond of FIG. 1(A) and a large proportion of the deep red parts. Many rates of the deep red parts are because the inner reflection volume is small and the color (black) of the ground of the diamond placing part gives influences, and means that the brightness is less as much. Further, the circumference is seen as an unevenly broken-off black, and the light does not assume the inner reflection in these black broken parts, and since it penetrates to the side of the diamond placing part as it is, the color (black) of the ground of the placing part is seen, and these parts therefore do not shine at all. The diamond of this photograph is wholly irregular in the pattern, not showing any "arrow" as seen in the photograph (A).

FIG. 2(A),(B) are photographs in which the diamonds shown in FIG. 1(A),(B) are turned over and observed from the rear sides thereof. Also in this case, although the diamond ideally cut shown in the photograph (A) has a high proportion of the white and the light red parts, the diamond of the inferior cut shown in the photograph (B) has the lower proportions of the white and the light red parts, and has high proportions of the deep red parts. Furthermore, in the diamond of the photograph (A), eight "heart shapes" radially extending from its center are acknowledged, and the patterns are symmetrical, while "heart shapes" as seen in the photograph (A) are scarcely seen in the photograph (B), and the patterns are not regular.

Thus, using the inventive instrument, the degree of the diamond brilliancy can be judged at a glance with the patterns when observed.

The principle based upon which the diamond takes the clear patterns as said above, is not always apparent in the present instrument, but it may be assumed that the light applying to the diamond is appropriately controlled with the lower tubular portion thereof and the upper tubular portion of the semi-transparent substance.

The inventor conducted the experiments mentioned below with diamonds of good cuts and bad ones of the same carat number for confirming the functions and effects of this invention.

First, a diamond 2 was positioned on the bottom of a funnel shaped vessel 1 with a black inner surface as shown in FIG. 3(1), and was observed from its upper part. In this case, the diamond of the good cut was seen large, and that of the bad one was seen small.

Next, the diamond 2 was positioned on the bottom of a tubular vessel 3 with the black inner surface as shown in FIG. 3(2), and was observed from its upper part in the same way. The tubular vessel 3 was used, which had an angle 15° between the line combining the center of its bottom to the upper end edge, and the axial line of the tubular vessel. In this case, as similarly in said funnel shaped vessel, the diamond of the good cut was seen large, and that of the bad one was seen small, and further in the good cut diamond, the right "arrows" as in the photograph of FIG. 1(A) were faintly seen. When a magnifying lens was provided on the upper end of the tubular vessel 3 and the diamond was observed, said "arrows" were more clearly seen. However in any of the observations, the fine patterns as seen in the photographs of FIG. 1 could not be observed.

A white semi-transparent tubular body 4 made of a synthetic resin was provided to said tubular vessel 3 on its upper part as shown in FIG. 3(3), and the diamond positioned at the bottom of the tubular vessel 3 was observed. As a result, the patterns corresponding to those of the photograph in FIG. 1 clearly appeared, and in the good cut diamond, said "arrows" could be observed very clearly. Moreover, when the magnifying lens was equipped on the upper end of the semi-transparent tubular body 4, the patterns could be more clearly observed.

The patterns which were then observed were composed of a white, several sorts of greys different in brightness and a black, since the inner circumference of the tubular vessel 3 was black, and the good cut diamond was clear in the configuration of its main body, and besides the white parts and the bright grey parts had a very high proportion as a whole. On the other hand, the bad cut diamond was observed in that the circumferential part of the diamond main body was as unevenly broken-off black and the proportion of the whole parts was low, while the proportion of the dark grey parts was high.

It was clear from the above experiments that the semi-transparent tubular body 4 placed above the tubular vessel 3 appropriately controlled the volume of the light entering the interior of the tubular vessel 3, whereby it contributed to the appearance of said patterns. It was assumed that the semi-transparent tubular body 4 basically served to gather the light into the tubular vessel 3 by diffused reflections therewithin, and that when direct sunlight from the outside was strong, the tubular body 4 served to appropriately limit it and to make uniform the light going into the tubular vessel 3.

Further, when the diamond observation tests were made on the instruments as shown in FIG. 3(3) where size ratios (inner diameter/height) of the tubular vessel 3 were variously changed, it was found that if an angle $\alpha$ between the line combining the center of the inner bottom as the diamond placing part of the tubular vessel 3 and the upper end edge of the tubular vessel 3, and the axial line of the tubular vessel was outside the range of 10° to 25°, the above mentioned patterns were difficult to see. That is if said angle $\alpha$ less than 10°, the whole of the diamond was seen blackish, and even the patterns of the good cut diamond as shown in the photograph (A) of FIG. 1 were not clearly tangible. If the angle $\alpha$ exceeded 25°, reversely, the whole part of the diamond was seen shining and the patterns were also intangible in this case. It is assumed that, if said angle $\alpha$ was too large (the inner diameter of the tubular vessel 3 was too large with respect to the height), the volume of the light directly applying to the diamond from the tubular body 4 was too much, and on the other hand, if the angle was too small (the inner diameter of the tubular vessel 3 was too small with respect to the height), the volume of the light was too small, and thus each of the cases did not achieve the appearance of the above mentioned patterns which required the delicate light volume. In other words, the volume of the light directly applying to the diamond from the tubular body 4 was considered to have a close relationship with the appearance of the patterns. As a result of the experiments, it was found that the most bright patterns appeared when the above angle $\alpha$ was 15° to 20°, especially about 15°, irrespective of the size of the tubular vessel 3.

It is therefore desirable in the inventive instrument to determine the angle $\alpha$ between the line combining the center of the inner bottom of the lower tubular portion or the outer tubular portion thereof (explanations will be made with the example of the lower tubular portion hereinafter) and its upper end edge, and the axial line of the lower tubular portion to be 10° to 25°, preferably 15° to 20°, irrespective of the embodiment of the structure, the size and others. As far as the present instrument satisfies such conditions, the size is not limited, for example, the whole of the instrument may be made as large as a thumb.

With the instrument of the invention, the pattern colors of the diamonds to be observed differ according to the colors of the inner circumferential surfaces of the lower tubular portion.

If the color of the inner circumferential surface of the lower tubular portion is black as the above stated experiments the light incident into the lower tubular portion scarcely reflects on the inner circumferential surface thereof, and the diamond shines only with the light directly applied from the upper part of the lower tubular portion, and the patterns to be observed with the naked eye are achromatic colors such as white-grey (several sorts of the greys different in brightness)black.

On the other hand, if the inner circumferential surface of the lower tubular portion is made chromatic as red, a part of the light going into the lower tubular portion reflects on the inner circumferential surface thereof, and then collides against the diamond, so that the patterns to be observed with the naked eye are made chromatic, tinged with color tones of the inner circumferential surface of the lower tubular portion, with respect to the parts excepting the white and the black. For example, if the inner circumference of the lower tubular portion is red, the patterns of the diamond to be observed are white-red (some kinds of colors different in the color tones and brightness such as pink, red, deep red or the like)-black.

Since the diamond placing part is black or blackish as mentioned below, it is desirable to make the inner circumference surface of the lower tubular portion chromatic in order to distinguish the patterns more clearly. In addition, if the inner circumference surface of the lower tubular portion is such a color reflecting the light, the light enters, as shown in FIG. 5, the diamond from the direction of about 180° of the upper side of the diamond by the light reflection in the inner circumference surface of the lower tubular portion, so that it is possible to observe more fine patterns in accordance with the inner reflecting conditions of the diamond in comparison with the case where the inner circumference surface is black as said above.

Moreover if the inner circumference is fluorescent among the chromatic colors, the bright patterns are especially available.

The diamond placing part should be black or blackish with less light reflection to distinguish clearly the parts of no inner reflection and not to permit the light reflecting from the diamond placing part to go into the lower part or the bottom of the diamond.

At the same time, it is found that the whole of the upper tubular portion or at least the upper part of the present instrument is shaped conical-trapezoidal, thereby to adjust the entering light volume and enable clearer distinction of the diamond. By structuring the upper tubular portion in such a shape, the upper tubular portion of the white or milk-white color does not come in sight at observation, and also in this sense the diamond patterns may be effectively studied. It is sufficient that the whole of the upper tubular portion composed of the semi-transparent material is shaped conical-trapezoidal, or its upper part only is shaped conical-trapezoidal and the lower part is tubular.

The upper tubular portion of such a structure is connected to a short tubular part or a brim whose lower edge is continued to the upper part of the lower tubular portion, and these parts do not disturb the observation or a later stated photographing if the inner bottom of said short tubular part or the upper surface of the brim is made black or blackish color with less light reflection.

If the inventive instrument has the structure provided with the observation magnifying lens on the upper end of the upper tubular portion composed of a semi-transparent material, enlarged diamond patterns may be studied, so that observation is very easy and the patterns are easily judged. On the other hand, with respect to the method of judging the diamond brilliance, for example, there is a case where it is desired that two or more diamonds of the same carat number are observed at the same time and are compared in their brilliance, and in such a case it is desirable to prepare a structure without a lens on the upper end of the upper tubular portion. That is, such an instrument allows a wide visual field due to the absence of the lens, and is suitable to concurrent observation of plural diamonds.

Such an inventive instrument reveals the diamond itself to be small in comparison with that having the lens, and is more or less inferior so much in the distinguishability of the patterns, however, the patterns may be sufficiently observed to an extent that the diamond patterns and brilliance may be compared among the diamonds.

The photographing method of the present invention is performed by means of the instrument without the lens. That is, the photographing is carried out by putting the lens of the camera close to the upper end of the tubular body or the inner tubular portion and directing the lens to the diamond positioned on the diamond placing part of the lower tubular portion or the outer tubular portion. It is possible thereby to take the photographs of the same patterns as viewed with the naked eye, using the above mentioned instrument equipped with the lens. FIGS. 1 and 2 are the photographs taken in this way. As a means of photographing, video camera or the like may be used besides general cameras.

It is of course possible to use the instrument whose upper tubular portion made of a semi-transparent material is a tubular body in a usual shape, but if such an instrument is used as said above which has the upper tubular portion whose whole or at least the upper part is composed in the conical-trapezoidal shape, the upper tubular portion is outside of the visual field of the camera. As a result, the upper tubular portion is not taken in the photograph itself, and also the clear patterns of the diamond may be photographed, since the light caused by the diffused reflection from the white upper tubular portion does not come to the camera lens.

When using an instrument having a camera rest on the upper end part of the upper tubular portion, the photographs may be more easily taken. In this instrument, the lens portion of a single-lens reflex camera and the like is placed on the camera rest, fitting the lens to the penetrating hole of the rest for photographing the diamond. Since the upper tubular portion is expanded outwardly in a conical-trapezoidal shape, it does not come into the view of the camera, and besides the upper surface of the camera rest and the inner bottom of the short tubular part or the upper part of the brim at the upper end part of the lower tubular portion is colored black or blackish with less light reflection, and only the diamond patterns may be photographed clearly and beautifully.

Further, this photographing may be similarly carried out by means of the instrument of such a structure where the upper tubular portion is not structured with the above mentioned conical-trapezoidal shape but with a tubular body of a larger diameter than that of the lower tubular portion and the camera rest is equipped on the upper end of the upper tubular portion. In this instrument, since the underside surface of the camera rest is composed of a white or a high bright color, the light is gathered appropriately within the lower tubular portion, and only the diamond patterns may be clearly photographed in the same way as the instrument of the upper tubular portion of a conical-trapezoidal shape.

In the photographing method according to the present invention, it is preferable to make the inner circumference surface of the lower tubular portion or the outer portion chromatic as red and to take color-photographs. If the lower tubular portion or the inner circumference surface of the lower tubular portion or the outer tubular portion is black or blackish color as stated above, the patterns becomes white-grey-black, but since the diamond placing part is black or blackish color, the distinguishability of the patterns in the photographs is slightly inferior. On the other hand, if the inner circumference surface of the lower tubular portion or the outer tubular portion is chromatic and monochromes are taken, it is difficult to distinguish the deep chromatic colors (e.g., deed red) composing the patterns from the black color of the foundation of the diamond placing part.

The thus taken photographs by the inventive method are very suitable to professional opinions of the diamonds. FIG. 6 (A),(B) are photographs of diamonds conventionally used for the professional opinions and the like (the photograph (A) is a good cut diamond and (B) is bad cut diamond). These photographs were taken in a manner that the diamonds were placed between the reflection sheet having the penetrating hole and the black sheet, and an illumination was applied to the diamonds from the oblique downward direction, and the diamonds were photographed by a camera through the penetrating hole from its upper side. In this photographing method, only the brightest parts and the least bright parts viewed with the naked eye are photographed as black, and other parts are whitish. Although the "arrows" are also seen in the photographs, they are black, which should be brightest actually. Ordinarily people could not visually perceive the correspondence between the patterns on the photographs and the actual diamond brilliance. Besides, the least bright parts also appear black, so that they could not distinguish them from the brightest parts. For example, the photograph of FIG. 6(B) shows black parts in the middle part between the center and the outer circumference, and it is impossible to distinguish whether these parts are the brightest parts or the least bright ones. Furthermore, other parts except the black ones hardly have light and shade, and are seen whitish as a whole. As seen from the photographs of FIG. 1, these parts should be brighter or have less bright parts, but their discrimination is scarcely possible. Accordingly, these photographs hardly produce stereoscopic effect as a whole. On the other hand, the patterns photographed by the present inventive method have, as shown in FIGS. 1 and 2, clear light and shade variation in good correspondence to the diamond brilliance, and have stereoscopic effect.

According to the inventor's confirmation, "heart shapes" seen in FIG. 2(A) have never appeared in the photographs taken by the prior art photographing method, even in black. That is, the patterns including "heart shapes" as shown in FIG. 2(A) have been enabled to be photographed by the present inventive method for the first time.

The photographing method of this invention may be, needless to say, practised by the instrument for exclusive use of photographing having a structure where the camera itself is incorporated in the above mentioned inventive instrument (that is, such a structure where the upper tubular portion and the lens part of the camera are made integral).

A further explanation will be made on the function of the inventive instrument having the outer tubular portion and the inner tubular portion of a semi-transparent substance.

In this instrument, the outer tubular portion corresponds to the lower tubular portion of the above mentioned instrument, and the inner tubular portion of this instrument similarly corresponds to the upper tubular portion of said instrument. Basic working effects are the same as those of the above mentioned instrument having the lower tubular portion and the upper tubular portion. Only, in the present instrument, since the inner tubular portion is slidable with respect to the outer tubular portion and can be housed therewithin, it is especially handy, and if the inner tubular portion is slid with respect to the outer tubular portion, the diamond can be alternately observed stepwise from the state close to the brilliance as viewed with the naked eye to the state revealing the patterns as shown in the above photographs.

That is, if the diamond is observed under the condition that it is positioned on the diamond placing part of the outer tubular portion, and the major part of the inner tubular portion is housed within the outer tubular portion, it is seen as bright nearly the same as when usually viewed with the naked eye (to an extent that the above eight "arrows" are seen subtly in the good cut diamond), since a light controlling function is not provided, which is to be effected by the semi-transparent inner tubular portion as FIG. 3(2). When the inner tubular portion is moved upward from this state, the semi-transparent inner tubular portion to provide serves the appearance of the patterns particular to the inventive instrument. In the instrument having the lens at the upper end part of the inner tubular portion, the observation is made sliding the inner tubular portion upward up to the position where the lens focuses on the diamond. In the instrument without the lens, the observation is done by sliding upward the inner tubular portion to an appropriate height.

Thus, according to the above mentioned instrument, said appearing mechanism of the patterns may be studied stepwise by gradually sliding the inner tubular portion upward from the inserted state within the outer tubular portion.

When the diamond is observed or photographed in a dark place by using the instrument of this invention, it is preferable to arrange an illumination at the outer side of the upper tubular portion or the inner tubular portion. But, when viewed with eyes, the patterns may be well observed even at a darker place.

Depending upon the above mentioned instrument of the present invention, it is possible to observe the diamond patterns in good correspondence to the brilliance, which has never been seen in the conventional art, and non-professionals could easily distinguish or judge the brightness degree according to the cuts and the proportions of the diamond.

In the photographs taken by the conventional art, there was a vital defect that the actually bright parts were taken black only and ordinary men could not visually perceive the correspondence to the diamond brightness, but by the photographing method of the present invention it is possible to take photographs of the diamonds having a good correspondence to the real brightness, and such photographs are very useful for the professional opinions or the like of the diamonds.

BRIEF DESCRIPTION OF THE DRAWINGS

FIGS. 3(1) to (3) are explanatory views showing experimental manners performed for confirming the effects of the present invention;

FIG. 4 is an explanatory view showing the basic structure of the inventive instrument;

FIG. 5 is an explanatory view showing the manner light applied to a diamond, in case the lower tubular portion of the inventive instrument is chromatic;

FIG. 7 is a side view, FIG. 8 is a plan view and FIG. 9 is a vertically cross sectional view;

FIG. 12 is a side view, FIG. 13 is a vertically cross sectional view, FIG. 14 is a cross sectional view along the line 14—14 of FIG. 12, and FIG. 15 is a vertically cross sectional view showing a condition where the inner tubular portion is extended;

FIGS. 21 and 22 show other structural examples of the lower tubular portion shown in FIG. 9 and others, where FIG. 21 shows perspective views of the disassembled lower tubular portion, and FIG. 22 is a perspective view showing that a base part is vertically turned over 180° from a state of FIG. 21;

FIGS. 23 and 24 show further structural examples of the lower tubular portion shown in FIG. 10 and others, where FIG. 23 shows perspective views of the disassembled lower tubular portion, and FIG. 24 is a perspective view showing that a connection part is vertically turned over 180° from a state of FIG. 23.

MOST PREFERABLE EMBODIMENTS FOR PRACTISING THE INVENTION

Figure 1A:
FIGS. 1(A),(B) and FIGS. 2(A),(B) show photographs of diamonds taken by means of the inventive instrument.
Figure 1B:
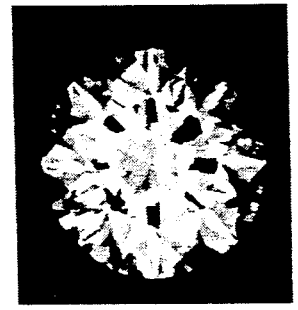
Figure 2A:
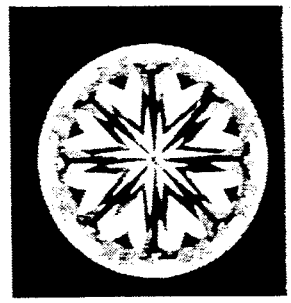
Figure 2B:
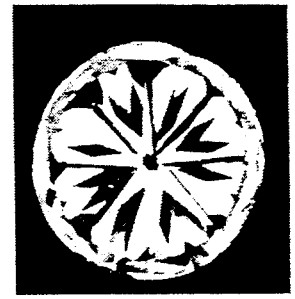
Figure 6A:
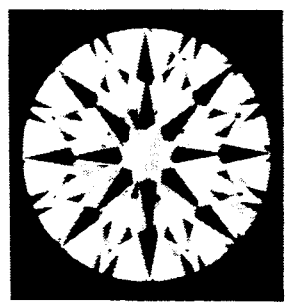
FIGS. 6(A),(B) show photographs of diamonds taken by means of a conventional photographing method.
Figure 6B:
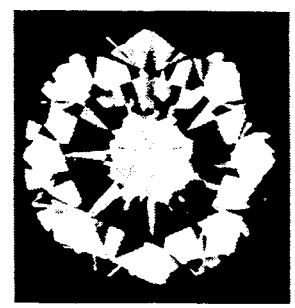
Figure 7:
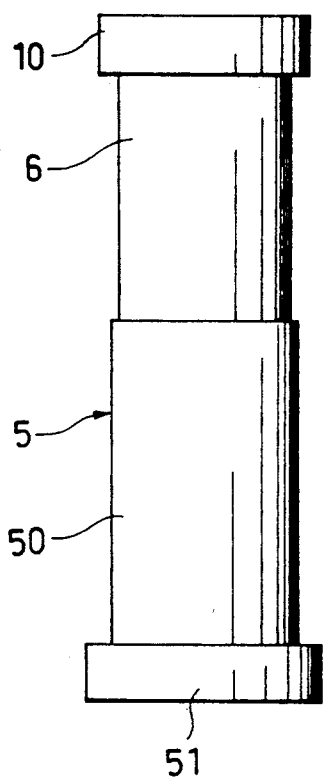
FIGS. 7 to 9 show one of the embodiments of the inventive instrument, where
Figure 9:
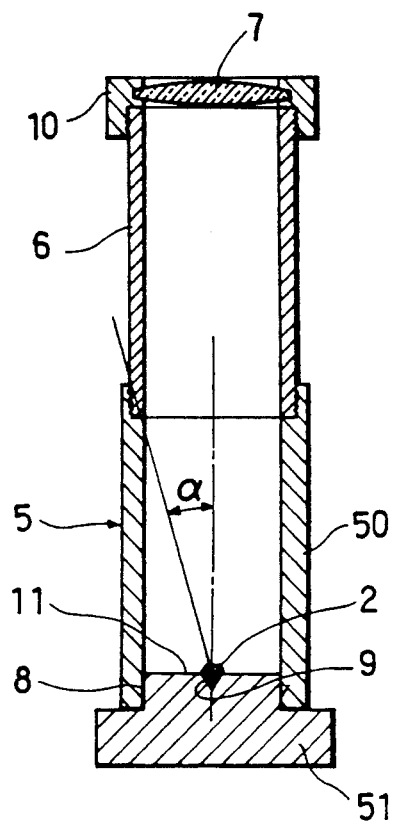
Figure 8:
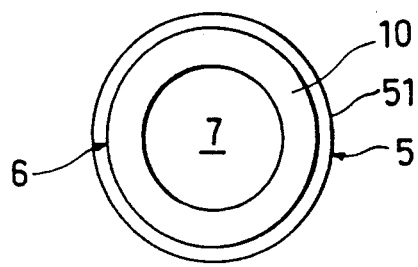

FIGS. 7 to 9 show one of the embodiments of the inventive instrument, where 5 designates a lower tubular portion, 6 is an upper tubular portion and 7 is an observation magnifying lens.

Said lower tubular portion 5 comprises a non-transparent substance, and is composed of a base part 51 and a main tubular body 50 detachably attached to said base part. The base part 51 has a circular step 8 at its upper part, and the lower part of the main tubular body 50 is detachably fitted onto said step 8. The upper surface of the base part 51 as the inner bottom of the main tubular body 50 is structured as a placing part 11 for placing a diamond. This placing part 11 is formed with a recess 9 for receiving the diamond.

The surface of the diamond placing part 11 is composed of a black or a blackish color for preventing irregular reflections of a light so as to clearly observe the diamond only.

Preferably, the inner circumference surface of the lower tubular portion 5 (tubular main body) is made black or blackish color with less light reflection, or chromatic color as red.

It is preferable that the lower tubular portion 5 has such a size ratio of inner diameter/height that the angle α is 10° to 25° (desirable 15° to 20°), which is made with an axial line of the lower tubular portion and a combining line between the center of the diamond placing part 11 (inner bottom part) and the upper end edge of the lower tubular portion.

Said upper tubular portion 6 is composed of a synthetic resin (e.g., polyethylene resin), or a white or milky white semi-transparent material such as glass, and is furnished on the upper end of the lower tubular portion 5 via a screwed part of a lower part thereof. It is sufficient that the upper tubular portion 6 has almost the same inner diameter and height as said lower tubular portion 5.

The lens 7 is supported by a holder ring 10 which is equipped via a screw at the upper end of the upper tubular portion 6. Therefore if the holder ring 10 is removed from the upper tubular portion 6, it may be used as an instrument without the lens.

The holding structure of the lens 7 is not limited to the present embodiment, but for example, such a structure may be provided where the holding ring is slided horizontally.

Figure 10:
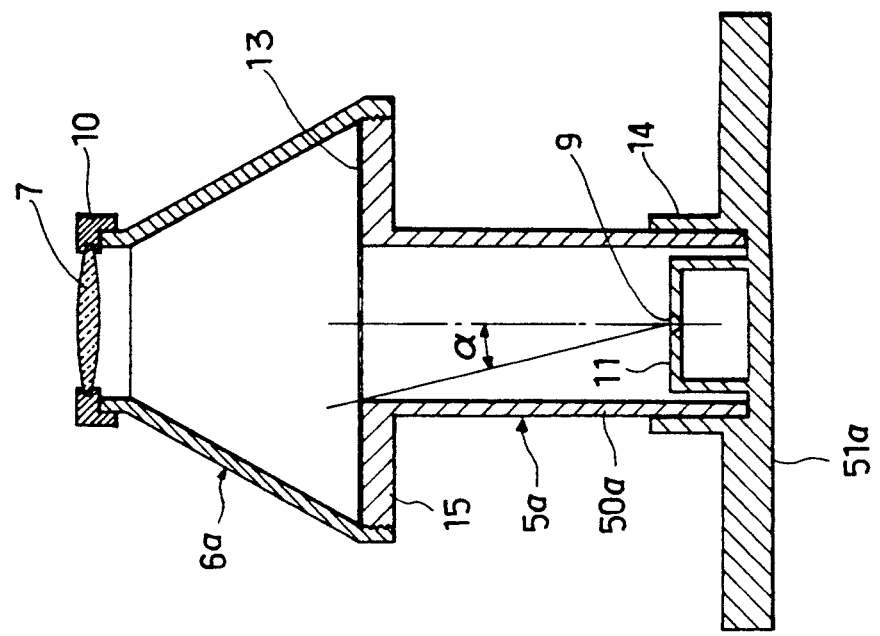
FIG. 10 is a vertically cross sectional view showing another embodiment of the present invention.

FIG. 10 shows other embodiment of the present invention, and an upper tubular portion 6a is composed in a conical-trapezoidal shape. The upper tubular portion 6a of a semi-transparent substance is made conical-trapezoidal, so that the light is adopted into the lower tubular portion 5a more properly, thereby to enable the availability of clearer diamond patterns, and since the upper tubular portion 6a does not come in sight when observing the diamond, only diamond patterns may be effectively studied.

The upper part of the lower tubular portion 5a continues to a short tubular portion 12 of a large diameter, and the lower part of the upper tubular portion 6a of the conical-trapezoidal shape is screwed on the upper part of the short tubular portion 12.

The lower tubular portion 5a is composed of a tubular body 50a and a base part 51a in a disc shape, and the tubular body 50a is inserted detachably into the interior of the ring 14 implanted in the center of the base 51a.

The inner bottom of the short tubular portion 12 is composed of a black or a blackish color with less light reflection so that the short tubular portion 12 does not prevent the observation. In the present embodiment, a black cloth 13 with less light reflection is especially adhered to the inner surface thereof.

Other structure are the same as those of FIGS. 7 to 9.

Figure 11:
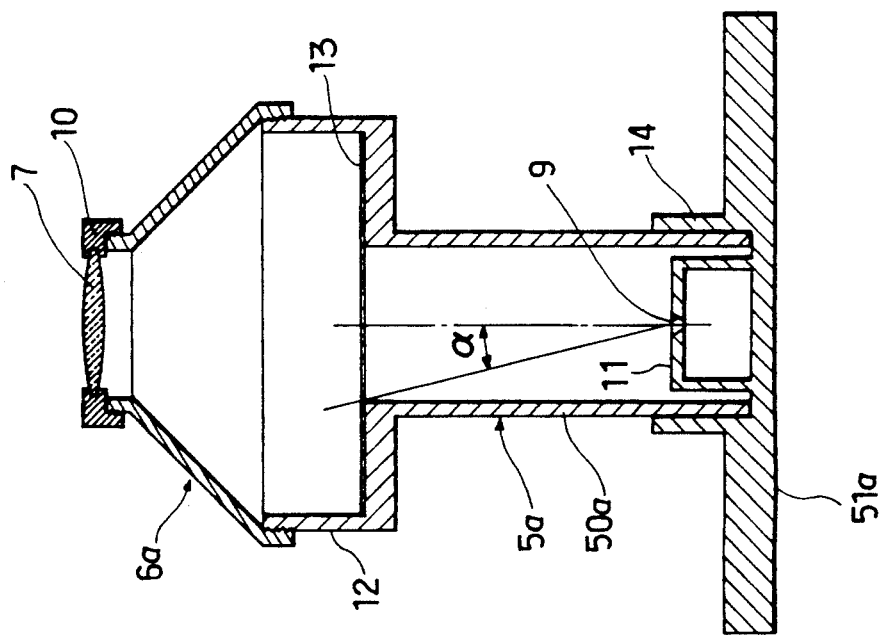
FIG. 11 is a vertically cross sectional view showing a further embodiment of the present invention.
Figure 12:
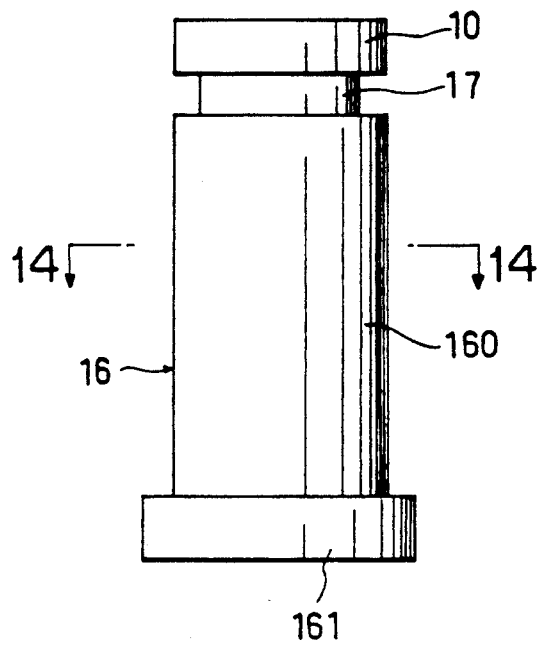
FIGS. 12 to 15 show a still further embodiment of the inventive instrument, where

FIG. 11 shows that the upper tubular portion 6a is composed to be conical similarly to the embodiment of FIG. 10, and in this embodiment, the upper tubular portion 6a is furnished to a brim 15 continued to the upper part of the lower tubular portion 5a. The upper surface of the brim 15 is also sticked with the black cloth 13.

Other structures are the same as those of said embodiments.

FIGS. 12 to 15 show an embodiment where an instrument is telescopic, and the reference numeral 16 is an outer tubular portion and 17 is an inner tubular portion.

Said outer tubular portion 16 comprises a non-transparent substance, and is composed of a base part 161 and a main tubular body 160 detachably attached to said base part. The base part 161 has a circular step 8 at its upper part, and the lower part of the main tubular body 160 is detachably fitted onto said step 8. The upper surface of the base part 161 as the inner bottom of the main tubular body 160 is structured as a part 11 for placing a diamond. This diamond placing part 11 is formed with a recess 9 for receiving the diamond.

Similarly to said embodiment, the surface of the placing part 11 is composed of a black or a blackish color for preventing irregular reflections of a light so as to clearly observe the diamond only. Preferably, the inner circumference surface of the lower tubular portion 16 (main tubular body) is made black or blackish color with less light reflection, or chromatic colors as red. Further, it is also preferable that the lower tubular portion 16 has such a size ratio of inner diameter/height that the angle α is 10° to 25° (desirably 15° to 20°), which is made with an axial line of the outer tubular portion and a combining line between the center of the diamond placing part 11 (inner bottom part) and the upper end edge of the lower tubular portion Said inner tubular portion 17 is composed of a synthetic resin (e.g. polyethylene resin), or a white or milky white semi-transparent material such as glass, and the inner tubular portion 17 is inserted therein slidably vertically from the upper edge of the outer tubular portion 16 and it is held at a desired height with respect to the outer tubular portion 16. It is sufficient that the inner tubular portion 17 has almost the same inner diameter and height as said outer tubular portion 16.

Similarly to said embodiment, the lens 7 is supported by a holder ring 10 which is furnished via a screw at the upper end of the inner tubular portion 17. Therefore if the holder ring 10 is removed from the inner tubular portion 17, it may be used as an instrument without the lens.

Also in this case, as a holding structure of the lens 7, for example, such a structure may be provided where the holding ring is slided horizontally.

This instrument is handy, since the inner tubular portion 17 can be slided vertically with respect to the outer tubular portion 16 and may be housed therewithin, and in addition when the inner tubular portion 17 is slided on the outer tubular portion 16, it is possible to alternately observe the state of almost the same brilliance as viewed with the naked eye and the state showing the patterns as seen in the above stated photographs.

Figure 13:
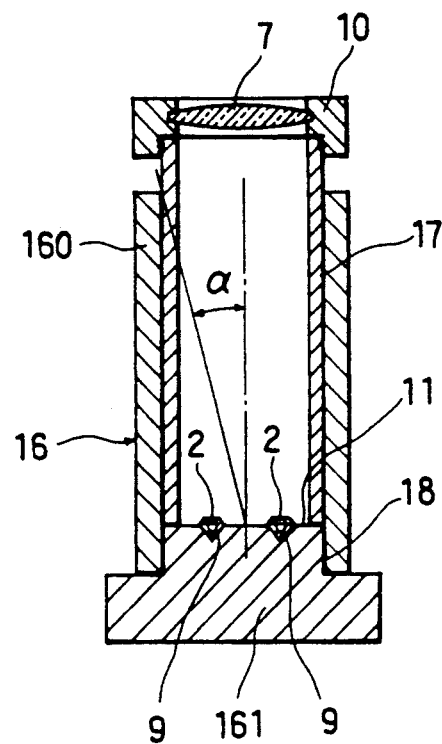
Figure 14:
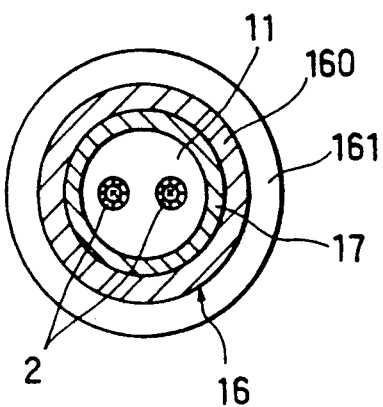
Figure 15:
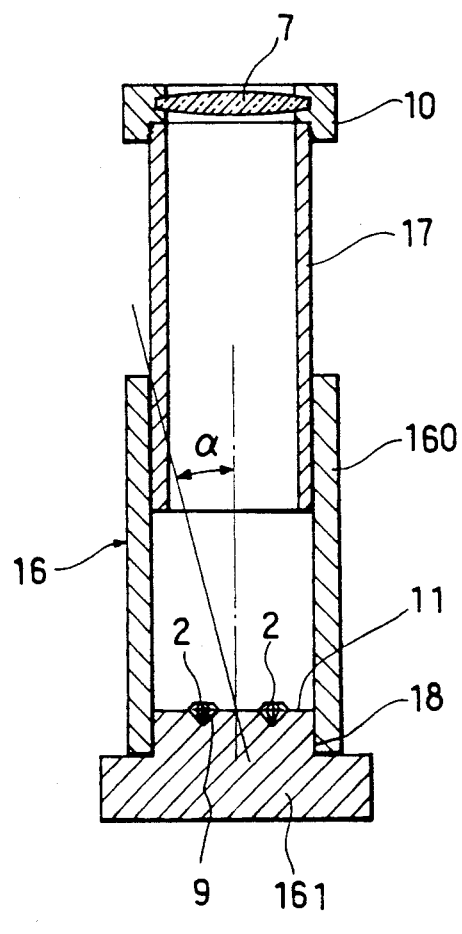

That is, as shown in FIG. 13, the diamonds 2 are positioned in the diamond placing part 11 of the inner tubular portion 17, and when observing the diamonds therewith under a condition that the major part of the inner tubular portion 17 is housed within the outer tubular portion 16, the diamonds 2 are seen almost in the same brilliance as normally viewed with the naked eye, since the inner tubular portion 17 does not function. When the inner tubular portion 17 is brought upward from this state, the patterns particular to the inventive instrument appear due to the function of the semi-transparent inner tubular portion 17, and as shown in FIG. 15, the inner tubular portion 17 is slided until the lens 7 at the upper end of the inner tubular portion 17 focuses on the diamonds 2, and the observation is carried out.

Figure 16:
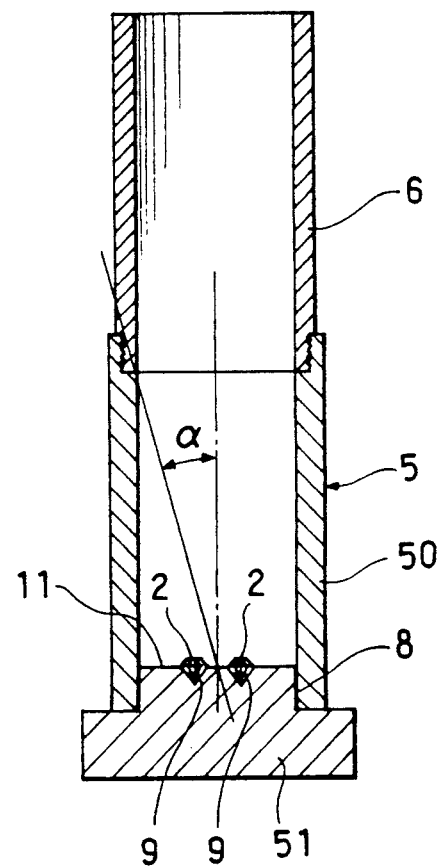
FIG. 16 is a vertically cross sectional view showing another embodiment of the invention.

FIG. 16 is the embodiment of an instrument of a structure having no lens at the upper end part of the upper tubular portion and other structures are the same as the embodiments of FIGS. 7 to 9.

There are sometimes cases of appreciating the diamond brilliance, for example, observing concurrently more than two diamonds of the same carat number for comparing their brilliance. The instrument of the present example is suitable to the concurrent observation of the multiple diamonds, since the field of view is widened as much as the absence of the lens.

In this instrument, the diamond itself is seen small in comparison with the instrument equipped with the lens as shown in FIGS. 7 to 9, and although its distinguishability of the pattern is more or less inferior as much, the diamond pattern can be sufficiently distinguished to the extent that the diamonds are mutually compared with each other as mentioned above.

Figure 17:
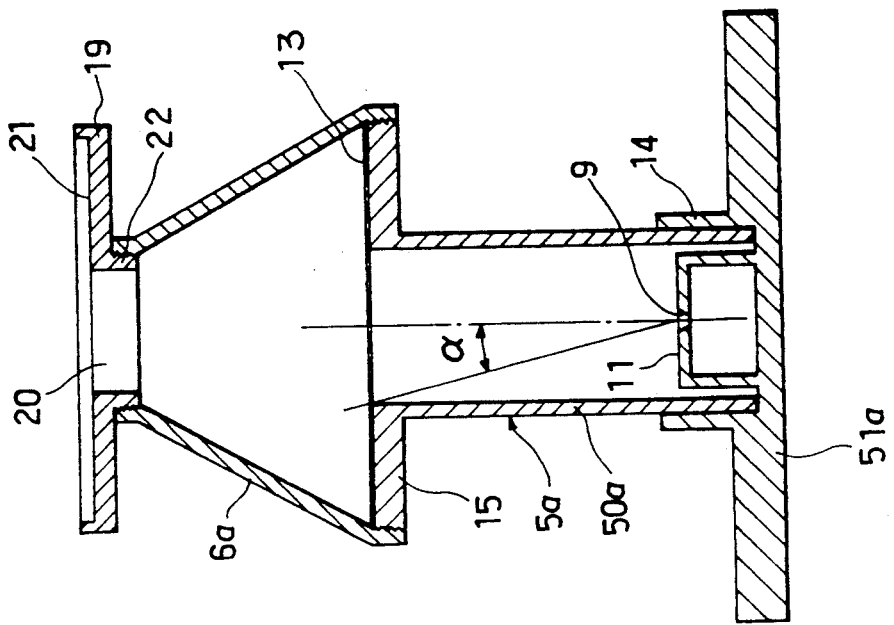
FIG. 17 is a vertically cross sectional view showing another embodiment of the invention.
Figure 18:
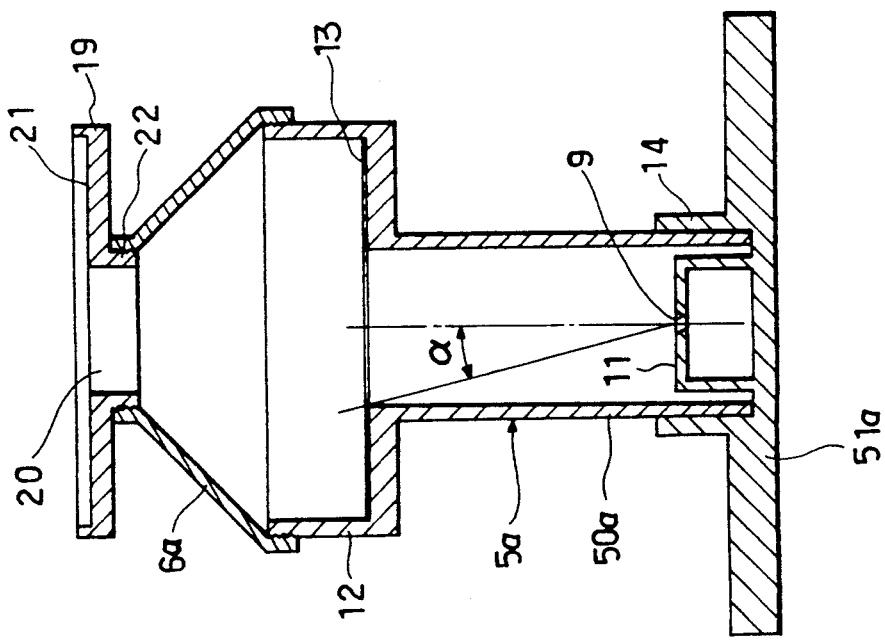
FIG. 18 is a vertically cross sectional view showing another embodiment of the invention.

FIGS. 17 and 18 show embodiments of such structure having no lens on the upper end of the upper tubular portion, respectively, and other basic structures are the same as the embodiment of FIGS. 10 and 11.

These embodiments are used for taking photographs, so camera rests 19 are provided on the upper ends of the upper tubular portions 6a. The camera rest 19 has a penetrating hole 20 at its center, and is placed on the upper end of the upper tubular portion 6a via a ring screw part 22 formed at the lower part of the penetrating hole.

The upper surface 21 (at least the circumferential part of the penetrating hole for receiving the camera) of the camera rest 19 is composed of a black or a blackish color with less light reflection.

In the structure having such a camera rest 19, it is preferable that the underside surface 191 of the camera rest has the white or a high brightening color, (e.g., whitish colors), so that the light may be introduced into the lower tubular portion 5a.

Figure 19:
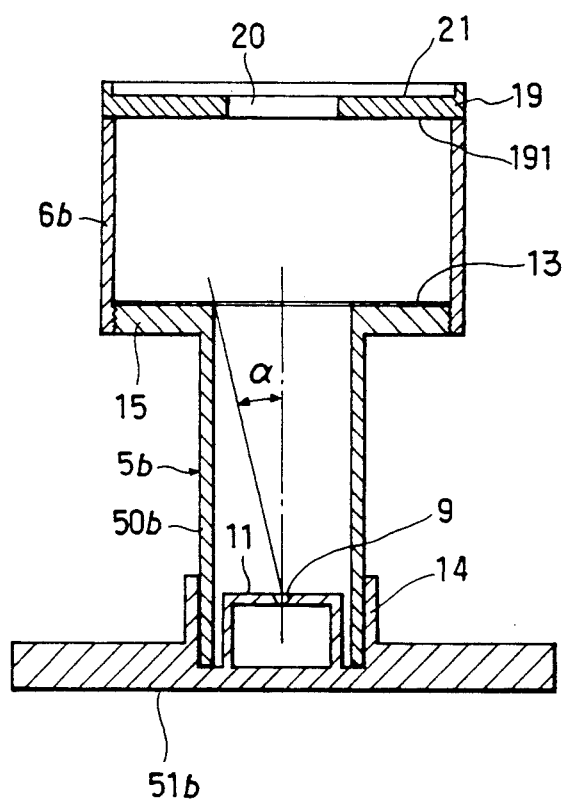
FIG. 19 is a vertically cross sectional view showing another embodiment of the invention.

FIG. 19 shows another embodiment of the inventive instrument having the camera rest where an upper tubular portion 6b is structured to be a larger diametered tubular body than a lower tubular portion 5b, and the camera rest 19 is furnished on the upper end of the upper tubular portion 6b of a large diameter.

In such a structure, the underside surface 191 of the camera rest 19 is especially a white or a high bright color (e.g., whitish colors) for adopting the light appropriately. Other structures of the tubular body 50b, the base part 51b, etc. are the same as those of the above mentioned embodiments.

Figure 20:
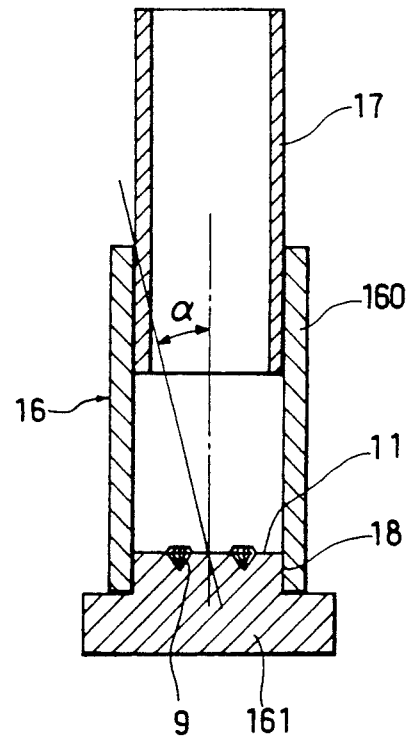
FIG. 20 is a vertically cross sectional view showing another embodiment of the invention.

FIG. 20 is an embodiment of an instrument having a structure without a lens on the upper end of the inner tubular portion 17, and other structures are the same as those of the embodiments of FIGS. 12 to 15.

In each of the above embodiments, the diamond placing part 11 may have recess portion 9 of an optional number, and be formed with a groove for inserting finger rings instead of the recess portion.

FIGS. 21 and 22 show other structural examples of the lower tubular portions shown in FIGS. 7 to 9, FIGS. 16 to 20 (or the outer tubular portions shown in FIGS. 12 to 15), which are structured for applying one instrument to both observations of bare stones and the finger rings.

Namely, a base part 51 composing the lower tubular portion 5 has the diamond placing parts 11A,11B, and fitting grooves 23A,23B for detachably inserting the lower part of the tubular body 50 at its upper and lower surfaces of the base part respectively.

The diamond placing part 11A at one side of the base part 51 is, as shown in FIG. 21, formed with a finger ring holder 24 having a groove 25 for inserting the ring part of the finger ring. The ring holder 24 is to be attached with a cover 26 having the recess 9 for placing the diamond. On the other hand, the placing part 11B at the other side of the base part 51 has a plain surface 27 as seen in FIG. 22. This plain surface 27 is used for studying the diamond from its rear side, whereby the table side thereof is placed downward.

The above stated structure may be applied to the outer tubular portions shown in FIGS. 12 to 15 in the same manner.

FIGS. 23 and 24 show one structural example of the lower tubular portions shown in FIGS. 10, 11, 17, 18 and 19, which may be applied to both observations of bare stones and finger rings in the same way as above mentioned.

In this embodiment, the base part 51a composing lower tubular portion 5a is composed of a table part 29 and a short tubular connection part 28 to be detachably attached to the table part 29. Said table part 29 has an insertion hole 30 at the center of its upper surface, and the connection part 28 is optionally fitted into the insertion hole 30 at its both sides. The connection part 28 has the same structure as the base part 51 of FIGS. 21 and 22.

According to such a structure, the desired side of the connection part 28 is inserted into the insertion hole 30 of the table part 29 in accordance with the fitting side of the placing part 11 of the connection part 28 to be used, and further the lower end of the tubular body 50a is inserted into the fitting groove 23A or 23B of the connection part 28.

In each of the above mentioned embodiments, the lower tubular portions 5, 5a, 5b, the upper tubular portions 6, 6a, 6b and the inner tubular portion 17 are all structured in a tubular shape, but the shapes are not especially limited, for example, they may be formed in polygon (octagon, ten angles, etc.).

Figure 25:
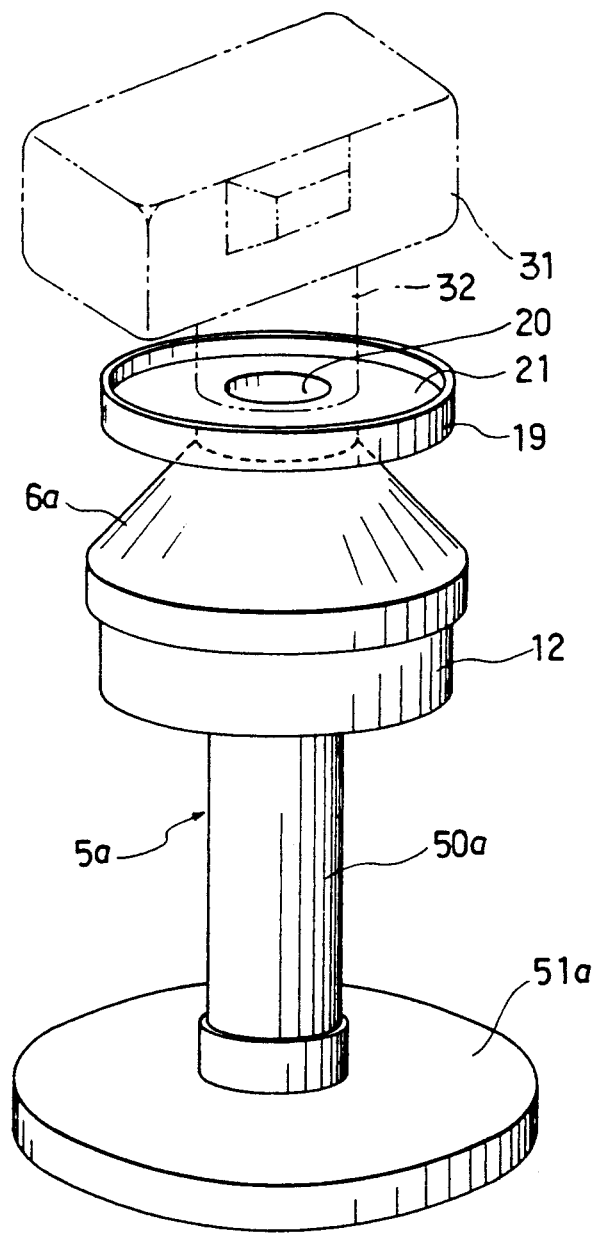
FIG. 25 is a perspective view showing one of the photographing arrangements of the present invention.

FIG. 25 shows one embodiment of the inventive photographing method by means of the instrument shown in FIG. 17.

The photographing according to the method of this invention is performed with the instrument without employing the magnifying observation lens, by bringing the lens of the camera or others (in a case of the camera, a close-up lens) close to the upper end part of the upper tubular portion or the inner tubular portion and directing the lens toward the diamond positioned on the placing part of the lower tubular portion or the outer tubular portion.

When the instrument having the camera rest 19 as shown in FIG. 25 is used, for example, the single-lens reflex camera 31 is mounted on the camera rest 19, the lens portion 32 thereof being met to the penetrating hole 20, and the diamond is photographed. Since the upper tubular portion 6a expands outwardly in a conical-trapezoidal shape, the instrument does not come within the visual field, and the upper surface of the camera rest 19 and the inner bottom of the short tubular part 12 is black or blackish color with less light reflection, so that only the diamond patterns may be photographed clearly and beautifully.

INDUSTRIAL APPLICABILITY

The instrument of this invention may be applied as a means to have the purchasers confirm the cuts and proportions of the diamonds when diamonds are sold at the jewelry shops.

The photographing method of this invention may be used for taking photographs or the like to be recorded in professional opinions of the diamonds.

What is claimed is:

1. An observing instrument for observing the brilliance of jewels such as diamonds, composed of
    a lower tubular portion composed of a material not permitting the passage of light, said lower tubular portion having an inner portion for receiving a jewel to be observed, and having an upper part,
    an upper tubular portion having a main body comprising a semi-transparent substance, said upper tubular portion being positioned on said upper part of said lower tubular portion, said upper tubular portion having an upper end part, and
    an observation magnifying lens mounted on the upper end part of said upper tubular portion,
    wherein the surface of the inner bottom part of said lower tubular portion is black or a blackish color with less light reflection.

2. The instrument as claimed in claim 1, wherein the lower tubular portion is composed such that a combining line between the center of the inner bottom part of the lower tubular portion and the upper edge part thereof has an angle from 10° to 25° with respect to the axial line of the lower tubular portion.

3. The instrument as claimed in claim 2, wherein the lower tubular portion is composed of a base part, the upper surface of which is for placing a jewel thereon, and a tubular body which is detachably attached on the upper part of said base part.

4. The instrument as claimed in claim 2, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is of black or a blackish color with less light reflection.

5. The instrument as claimed in claim 2, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

6. The instrument as claimed in claim 2, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

7. The instrument as claimed in claim 1, wherein the lower tubular portion is composed of a base part, the upper surface of which is form placing a jewel thereon, and a tubular body which is detachably attached on the upper part of said base part.

8. The instrument as claimed in claim 1, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

9. An observing instrument for observing the brilliance of jewels such as diamonds, composed of:
    an outer tubular portion comprising a material not permitting the passage of light, said outer tubular portion having an inner bottom portion for receiving a jewel to be observed,
    an inner tubular portion having a main body comprising a semi-transparent substance, said inner tubular portion being inserted slidably vertically into the interior of said outer tubular portion from the upper end thereof, and
    an observation magnifying lens mounted on said upper end part of said inner tubular portion,
    wherein the surface of the inner bottom part of said outer tubular portion is black or blackish color with less light reflection.

10. The instrument as claimed in claim 9, wherein the outer tubular portion is composed such that a combining line between the center of the inner bottom part of the outer tubular portion and the upper edge portion thereof has an angle from 10° to 25° with respect to the axial line of the outer tubular portion.

11. The instrument as claimed in claim 10, wherein the outer tubular portion is composed of a base part, the upper surface of which is a part for placing a jewel thereon and a tubular body which is detachably attached on the upper part of said base part.

12. The instrument as claimed in claim 9, wherein the outer tubular portion is composed of a base part, the upper surface of which is a part for placing a jewel thereon and a tubular body which is detachably attached on the upper part of said base part.

13. An observing instrument for observing the brilliance of jewels such as diamonds, composed of:

a lower tubular portion composed of a material not permitting the passage of light, said lower tubular portion having an inner bottom portion for receiving a jewel to be observed, and having an upper part, an upper tubular portion having a main body comprising a semi-transparent substance, said upper tubular portion being positioned on said upper part of said lower tubular portion, wherein the surface of the inner bottom part of said lower tubular portion is black or blackish color with less light reflection.

14. The instrument as claimed in claim 13, wherein the lower tubular portion is composed such that a combining line between the center of the inner bottom part of the lower tubular portion and the upper edge portion thereof has an angle from 10° to 25° with respect to the axial line of the lower tubular portion.

15. The instrument as claimed in claim 14, wherein the lower tubular portion is composed of a base part, the upper surface of which is for placing jewel thereon and a tubular body which is detachably attached on the upper part of said base part.

16. The instrument as claimed in claim 15, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

17. The instrument as claimed in claim 16, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

18. The instrument as claimed in claim 15, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

19. The instrument as claimed in claim 14, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

20. The instrument as claimed in claim 19, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

21. The instrument as claimed in claim 14, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or blackish color with less light reflection; at least a circumferential part around the penetrating hole at the upper surface of said camera rest is black or a blackish color with less light reflection; and the underside of said camera rest is composed in white or a high bright color.

22. The instrument as claimed in claim 13, wherein the lower tubular portion is composed of a base part, the upper surface of which is for placing a jewel thereon and a tubular body which is detachably attached on the upper part of said base part.

23. The instrument as claimed in claim 22, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

24. The instrument as claimed in claim 23, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

25. The instrument as claimed in claim 22, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

26. The instrument as claimed in claim 13, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

27. The instrument as claimed in claim 26, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

28. The instrument as claimed in claim 13, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

29. An observing instrument for observing the brilliance of jewels such as diamonds, composed of:
an outer tubular portion composed of a material not permitting the passage of light, said outer tubular portion having an inner bottom portion for receiving a jewel to be observed, and having an upper end,
an inner tubular portion having a main body comprising a semi-transparent substance, said inner tubular portion being inserted slidably vertically into the interior of said outer tubular portion from the upper end thereof,
wherein a surface of the inner bottom part of said outer tubular portion is black or a blackish color with less light reflection.

30. The instrument as claimed in claim 29, wherein the outer tubular portion is composed such that a combining line between the center of the inner bottom part of the lower tubular portion and the upper edge part thereof has an angle from 10° to 25° with respect to the axial line of the lower tubular portion.

31. The instrument as claimed in claim 30, wherein the outer tubular portion further comprises a base part having an upper surface and a tubular body detachably attached to said upper surface, the upper surface being adapted to receive a jewel thereon.

32. The instrument as claimed in claim 29, wherein the outer tubular portion further comprises a base part having an upper surface and a tubular body detachably attached to said upper surface, the upper surface being adapted to receive a jewel thereon.

33. A method of photographing jewels such as diamonds, comprising:
providing an observing instrument comprising:
a lower tubular portion comprising a material not permitting the passage of light, said lower tubular portion having an inner bottom portion for receiving a jewel to be observed, and having an upper part,
an upper tubular portion having a main body comprising a semi-transparent substance, said upper tubular portion being positioned on said upper part of said lower tubular portion, said upper tubular portion having an upper end part, and
an observation magnifying lens mounted on said upper end part of said upper tubular portion,
wherein the surface of the inner bottom part of said lower tubular portion is black or blackish color with less light reflection;
positioning a jewel on said inner bottom portion; and
directing the lens of a photographing machine toward said jewel from the upper direction of said upper tubular portion so as to photograph said jewel.

34. A method of photographing jewels such as diamonds, comprising:
providing an observing instrument comprising:
a lower tubular portion comprising a material not permitting the passage of light, said lower tubular portion composed of a material not permitting the passage of light, said lower tubular portion having an inner bottom portion for receiving a jewel to be observed, and having an upper part,
an upper tubular portion having a main body comprising a semi-transparent substance, said upper tubular portion being positioned on said upper part of said lower tubular portion,
wherein the surface of the inner bottom part of said lower tubular portion is black or blackish color with less light reflection;
positioning a jewel on said inner bottom portion; and
directing the lens of a photographing machine toward said jewel from the upper direction of said upper tubular portion so as to photograph said jewel.

35. The method according to claim 34, wherein said lower tubular portion is composed such that a combining line between the center of the inner bottom part of the lower tubular portion and the upper edge portion thereof has an angle from 10° to 25° with respect to the axial line of the lower tubular portion.

36. The method according to claim 35, wherein the lower tubular portion is composed of a base part, the upper surface of which is for placing a jewel thereon and a tubular body which is detachably attached on the upper part of said base part.

37. The method according to claim 36, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

38. The method according to claim 37, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

39. The method of claim 36, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

40. The method according to claim 35, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

41. The method according to claim 40, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

42. The method of claim 35, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

43. The method according to claim 34, wherein the lower tubular portion is composed of a base part, the upper surface of which is for placing a jewel thereon and a tubular body which is detachably attached on the upper part of said base part.

44. The method of claim 43, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

45. The method according to claim 34, wherein at least an upper part of said upper tubular portion is structured in a conical-trapezoidal shape, and a lower end thereof is connected to a short tubular part of a large diameter or a brim part, which is connected to the upper part of the lower tubular portion, and the inner bottom surface of said short tubular part or the upper surface of said brim part is black or a blackish color with less light reflection.

46. The method according to claim 45, wherein at least an upper part of said upper tubular portion is structured in a conical-trapezoidal shape, and a lower end thereof is connected to a short tubular part of a large diameter or a brim part, which is connected to the upper art or the lower tubular portion, and the inner bottom surface of said short tubular part or the upper surface of said brim part is black or a blackish color with less light reflection.

47. The method according to claim 45, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

48. The method according to claim 45, wherein a camera rest having a penetrating hole at the center thereof and a circumferential part around said penetrating hole is connected to the upper end part of the upper tubular portion, and at least the circumferential part around the penetrating hole on the upper surface of said camera rest is black or a blackish color with less light reflection.

49. The method of claim 34, wherein the upper tubular portion is structured to be larger in diameter than the lower tubular portion; the lower end thereof is connected to a short tubular part of a large diameter or a brim part mounted on the upper part of the lower tubular portion; a camera rest having a penetrating hole at its center is connected on the upper end part of the upper tubular portion; the inner bottom surface of said short tubular part or the upper surface of the brim part are black or a blackish color with less light reflection; at least a circumferential part around the penetrating hole at the upper surface of said camera rest is black or a blackish color with less light reflection; and the underside of said camera rest is composed in white or a high bright color.

50. A method of photographing jewels such as diamonds, comprising:
    providing an observing instrument comprising:
    an outer tubular portion composed of a material not permitting the passage of light, said outer tubular portion having an inner bottom portion for receiving a jewel to be observed, and having an upper end,
    an inner tubular portion having a main body comprising a semi-transparent substance, said inner tubular portion being inserted slidably vertically into the interior of said outer tubular portion from the upper end thereof,
    wherein a surface of the inner bottom part of said outer tubular portion is black or a blackish color with less light reflection;
    positioning a jewel on said inner bottom portion; and
    directing the lens of a photographing machine toward said jewel from the upper direction of said inner tubular portion so as to photograph said jewel.

51. The method according to claim 50, wherein the outer tubular portion is composed such that a combining line between the center of the inner bottom part of the lower tubular portion and the upper edge part thereof has an angle from 10° to 25° with respect to the axial line of the lower tubular portion.

52. The method according to claim 51, wherein the outer tubular portion further comprises a base part having an upper surface and a tubular body detachably attached to said upper surface, the upper surface being adapted to receive a jewel thereon.

53. The method according to claim 50, wherein the outer tubular portion further comprises a base part having an upper surface and a tubular body detachably attached to said upper surface, the upper surface being adapted to receive a jewel thereon.

* * * * *